(12) United States Patent
Stransky et al.

US010370725B2

(10) Patent No.: US 10,370,725 B2
(45) Date of Patent: Aug. 6, 2019

(54) FGR FUSIONS (71) Applicant: BLUEPRINT MEDICINES CORPORATION, Cambridge, MA (US)

(72) Inventors: Nicolas Stransky, Charlestown, MA (US); Ethan G. Cerami, Winchester, MA (US)

(73) Assignee: Blueprint Medicines Corporation, Cambridge, MA (US)

( * ) Notice: Subject to any disclaimer, the term of this patent is extended or adjusted under 35 U.S.C. 154(b) by 0 days.

(21) Appl. No.: 15/326,368

(22) PCT Filed: Jul. 15, 2015

(86) PCT No.: PCT/US2015/040553
§ 371 (c)(1),
(2) Date: Jan. 13, 2017

(87) PCT Pub. No.: WO2016/011141
PCT Pub. Date: Jan. 21, 2016

(65) Prior Publication Data
US 2017/0211149 A1    Jul. 27, 2017

Related U.S. Application Data

(60) Provisional application No. 62/025,854, filed on Jul. 17, 2014.

(51) Int. Cl.
*C12Q 1/68* (2018.01)
*C07H 21/04* (2006.01)
*C12Q 1/6886* (2018.01)
*C12N 15/113* (2010.01)

(52) U.S. Cl.
CPC ........ *C12Q 1/6886* (2013.01); *C12N 15/1138* (2013.01); *C12Q 2600/156* (2013.01)

(58) Field of Classification Search
None
See application file for complete search history.

(56) References Cited

FOREIGN PATENT DOCUMENTS

JP    2005052018    3/2005

OTHER PUBLICATIONS

International Patent Application No. PCT/US2015/040553, filed Jul. 15, 2015, by Blueprint Medicines Corporation: International Search Report and Written Opinion, dated Oct. 13, 2015.
GenBank Accession No. NM_005248, "*Homo sapiens* FGR protooncogene, Src family tyrosine kinase (FGR), transcript variant 1, mRNA" PRI May 14, 2017, 6 pages.
GenBank Accession No. NM_006990, "*Homo sapiens* WAS protein family member 2 (WASF2), transcript variant 1, mRNA" PRI Jun. 26, 2017, 6 pages.
Kim, et al. (2011) "Functional roles of Src and Fgr in ovarian carcinoma" *Clin Cancer Res.*, 17(7):1713-1721.

(Continued)

*Primary Examiner* — Jeanine A Goldberg
(74) *Attorney, Agent, or Firm* — Finnegan, Henderson, Farabow Garrett & Dunner, LLP (57) ABSTRACT

FGR (feline Gardner-Rasheed sarcoma viral oncogene homolog) fusions are described herein. Further provided are methods of diagnosing and treating diseases or disorders associated with FGR fusions, such as conditions mediated by FGR aberrant activity, or overexpression.

9 Claims, 7 Drawing Sheets

Specification includes a Sequence Listing.

(56) References Cited

OTHER PUBLICATIONS

Montero et al., (2011) "Inhibition of Src Family Kinases and Receptor Tyrosine Kinases by Dasatnib: Possible Combinations in Solid Tumors,"*Clin Cancer Res.*, 17(17): 5546-5552.
Soda, M. et al. (2007) "Identification of the transforming *EML4-ALK* fusion gene in non-small-cell lung cancer" *Nature*, 448:561-566.
Zuccato et al., (2006) "Sorting of fas ligand to secretory lysosomes is regulated by mono-ubiquitylation and phosphorylation," *Journal of Cell Science*, 20(1): 191-199.

FIG. 1

```
   1  GCCCAGGGCG GGGAATCGCG TAATGGCGGA CACAGGCAGG GCGAGCGCGG    50
  51  CTGGGGGCGT AGCGCGCTGA GGGGGTCCGG CCGTTTGGCA GCCCGCGAGG   100
 101  CGGTCCGCGG GAGCACACTC TGTGCGGAGA CTGGGCGGCC GGCCGACCCT   150
 151  TCCTGTCGCT GACGGCGACT GCGGGAGGCC AG/GTCTCTGA CCCCTCCCAA   200
 201  GGATCATGCC GCAGCCCCAC TGACCCAGGA GTAGGGGCCT AAGGGCAGGG   250
 251  AACCTGGAAT GGGCTGTGTG TTCTGCAAGA AATTGGAGCC GGTGGCCACG   300
 301  GCCAAGGAGG ATGCTGGCCT GGAAGGGGAC TTCAGAAGCT ACGGGGCAGC   350
 351  AGACCACTAT GGGCCTGACC CCACTAAGGC CCGGCCTGCA TCCTCATTTG   400
 401  CCCACATCCC CAACTACAGC AACTTCTCCT CTCAGGCCAT CAACCCTGGC   450
 451  TTCCTTGATA GTGGCACCAT CAGGGGTGTG TCAGGGATTG GGGTGACCCT   500
 501  GTTCATTGCC CTGTATGACT ATGAGGCTCG AACTGAGGAT GACCTCACCT   550
 551  TCACCAAGGG CGAGAAGTTC CACATCCTGA ACAATACTGA AGGTGACTGG   600
 601  TGGGAGGCTC GGTCTCTCAG CTCCGGAAAA ACTGGCTGCA TTCCCAGCAA   650
 651  CTACGTGGCC CCTGTTGACT CAATCCAAGC TGAAGAGTGG TACTTTGGAA   700
 701  AGATTGGGAG AAAGGATGCA GAGAGGCAGC TGCTTTCACC AGGCAACCCC   750
 751  CAGGGGGCCT TTCTCATTCG GGAAAGCGAG ACCACCAAAG GTGCCTACTC   800
 801  CCTGTCCATC CGGGACTGGG ATCAGACCAG AGGCGATCAT GTGAAGCATT   850
 851  ACAAGATCCG CAAACTGGAC ATGGGCGGCT ACTACATCAC CACACGGGTT   900
 901  CAGTTCAACT CGGTGCAGGA GCTGGTGCAG CACTACATGG AGGTGAATGA   950
 951  CGGGCTGTGC AACCTGCTCA TCGCCCCTG CACCATCATG AAGCCGCAGA   1000
1001  CGCTGGGCCT GGCCAAGGAC GCCTGGGAGA TCAGCCGCAG CTCCATCACG   1050
1051  CTGGAGCGCC GGCTGGGCAC CGGCTGCTTC GGGGATGTGT GGCTGGGCAC   1100
1101  GTGGAACGGC AGCACTAAGG TGGCGGTGAA GACGCTGAAG CCGGGCACCA   1150
1151  TGTCCCCGAA GGCCTTCCTG GAGGAGGCGC AGGTCATGAA GCTGCTGCGG   1200
1201  CACGACAAGC TGGTGCAGCT GTACGCCGTG GTGTCGGAGG AGCCCATCTA   1250
1251  CATCGTGACC GAGTTCATGT GTCACGGCAG CTTGCTGGAT TTTCTCAAGA   1300
1301  ACCCAGAGGG CCAGGATTTG AGGCTGCCCC AATTGGTGGA CATGGCAGCC   1350
1351  CAGGTAGCTG AGGGCATGGC CTACATGGAA CGCATGAACT ACATTCACCG   1400
1401  CGACCTGAGG GCAGCCAACA TCCTGGTTGG GGAGCGGCTG GCGTGCAAGA   1450
1451  TCGCAGACTT TGGCTTGGCG CGTCTCATCA AGGACGATGA GTACAACCCC   1500
1501  TGCCAAGGTT CCAAGTTCCC CATCAAGTGG ACAGCCCCAG AAGCTGCCCT   1550
1551  CTTTGGCAGA TTCACCATCA AGTCAGACGT GTGGTCCTTT GGGATCCTGC   1600
1601  TCACTGAGCT CATCACCAAG GGCCGAATCC CCTACCCAGG CATGAATAAA   1650
1651  CGGGAAGTGT TGGAACAGGT GGAGCAGGGC TACCACATGC CGTGCCCTCC   1700
1701  AGGCTGCCCA GCATCCCTGT ACGAGGCCAT GGAACAGACC TGGCGTCTGG   1750
1751  ACCCGGAGGA GAGGCCTACC TTCGAGTACC TGCAGTCCTT CCTGGAGGAC   1800
1801  TACTTCACCT CCGCTGAACC ACAGTACCAG CCCGGGGATC AGACATAGCC   1850
1851  TGTCCGGGCA TCAACCCTCT CTGGCGGTGG CCACCAGTCC TTGCCAATCC   1900
1901  CCAGAGCTGT TCTTCCAAAG CCCCAGGCT  GGCTTAGAAC CCCATAGAGT   1950
1951  CCTAGCATCA CCGAGGACGT GGCTGCTCTG ACACCACCTA GGGCAACCTA   2000
2001  CTTGTTTTAC AGATGGGGCA AAAGGAGGCC CAGAGCTGAT CTCTCATCCG   2050
2051  CTCTGGCCCC AAGCACTATT TCTTCCTTTT CCACTTAGGC CCCTACATGC   2100
2101  CTGTAGCCTT TCTCACTCCA TCCCCACCCA AAGTGCTCAG ACCTTGTCTA   2150
2151  GTTATTTATA AAACTGTATG TACCTCCCTC ACTTCTCTCC TATCACTGCT   2200
2201  TTCCTACTCT CCTTTTATCT CACTCTAGTC CAGGTGCCAA GAATTTCCCT   2250
2251  TCTACCCTCT ATTCTCTTGT GTCTGTAAGT TACAAAGTCA GGAAAAGTCT   2300
2301  TGGCTGGACC CCTTTCCTGC TGGGTGGATG CAGTGGTCCA GGACTGGGGT   2350
2351  CTGGGCCAG  GTTTGAGGGA GAAGGTTGCA GAGCACTTCC CACCTCTCTG   2400
2401  AATAGTGTGT ATGTGTTGGT TTATTGATTC TGTAAATAAG TAAAATGACA   2450
2451  ATATGAATCC TCAAACCATG AAAAAAAAAA AAAAAAA             2488
                                                    (SEQ ID NO:1)
```

FIG. 2

```
  1  MGCVFCKKLE  PVATAKEDAG  LEGDFRSYGA  ADHYGPDPTK  ARPASSFAHI   50
 51  PNYSNFSSQA  INPGFLDSGT  IRGVSGIGVT  LFIALYDYEA  RTEDDLTFTK  100
101  GEKFHILNNT  EGDWWEARSL  SSGKTGCIPS  NYVAPVDSIQ  AEEWYFGKIG  150
151  RKDAERQLLS  PGNPQGAFLI  RESETTKGAY  SLSIRDWDQT  RGDHVKHYKI  200
201  RKLDMGGYYI  TTRVQFNSVQ  ELVQHYMEVN  DGLCNLLIAP  CTIMKPQTLG  250
251  LAKDAWEISR  SSITLERRLG  TGCFGDVWLG  TWNGSTKVAV  KTLKPGTMSP  300
301  KAFLEEAQVM  KLLRHDKLVQ  LYAVVSEEPI  YIVTEFMCHG  SLLDFLKNPE  350
351  GQDLRLPQLV  DMAAQVAEGM  AYMERMNYIH  RDLRAANILV  GERLACKIAD  400
401  FGLARLIKDD  EYNPCQGSKF  PIKWTAPEAA  LFGRFTIKSD  VWSFGILLTE  450
451  LITKGRIPYP  GMNKREVLEQ  VEQGYHMPCP  PGCPASLYEA  MEQTWRLDPE  500
501  ERPTFEYLQS  FLEDYFTSAE  PQYQPGDQT                           529
                                                       (SEQ ID NO:2)
```

FGR FUSIONS

This application is a national stage application of and claims priority under 35 U.S.C. § 371 to International Application No. PCT/US2015/040553, filed Jul. 15, 2015, which claims the benefit of U.S. Provisional Application No. 62/025,854, filed Jul. 17, 2014, the contents of both of which are incorporated herein by reference in their entirety to provide continuity of disclosure.

The instant application contains a Sequence Listing which has been submitted electronically in ASCII format and is hereby incorporated by reference in its entirety. Said ASCII copy, created on Sep. 3, 2015, is named 12386.0010-00304_SL.txt and is 8,289 bytes in size.

FGR (feline Gardner-Rasheed sarcoma viral oncogene homolog) fusions are described herein. Further provided are methods of diagnosing and treating diseases or disorders associated with FGR fusions, such as conditions mediated by aberrant FGR expression or activity, or conditions associated with overexpression of FGR.

Many forms of cancer are caused by genetic lesions that give rise to tumor initiation and growth. Genetic lesions may include chromosomal aberrations, such as translocations, inversions, deletions, copy number changes, gene expression level changes, and somatic and germline mutations. Indeed, the presence of such genomic aberrations is a hallmark feature of many cancers, including, for example, B cell cancer, lung cancer, breast cancer, ovarian cancer, pancreatic cancer, and colon cancer. In some models, cancer represents the phenotypic end-point of multiple genetic lesions that endow cells with a full range of biological properties required for tumorigenesis.

Recent efforts by The Cancer Genome Atlas (TCGA), the International Cancer Genome Consortium (ICGC), and dozens of other large-scale profiling efforts have generated an enormous amount of new sequencing data for dozens of cancer types—this includes whole-genome DNA, whole-exome DNA, and full-transcriptome RNA sequencing. These efforts have led to the identification of new driver genes and fusion genes within multiple cancer types. Fusions, particularly fusions involving kinases, are of particular interest, as such fusions have been shown to be oncogenic, and have been successfully targeted by new therapeutics. For example, anaplastic lymphoma kinase (ALK), one of the receptor tyrosine kinases, is known to become oncogenic when fused with various genes. See, e.g., M. Soda et al, "Identification of the transforming EML4-ALK fusion gene in non-small-cell lung cancer," *Nature* 444:561-566 (2007).

A need exists for identifying novel genetic lesions associated with cancer. For example, the presence of fusions involving a kinase in samples collected from more than one source can indicate that the kinase is an oncogenic driver. The identification of such fusions can be an effective approach to diagnosis of cancers and development of compounds, compositions, methods, and assays for evaluating and treating cancer patients.

In one aspect, the present disclosure provides a method for detecting the presence of an FGR gene fusion in a biological sample. The method includes the steps of: (a) obtaining a biological sample from a mammal; and (b) contacting the sample with a reagent that detects an FGR gene fusion, to determine whether an FGR gene fusion is present in the biological sample. In some embodiments, the sample can be from, e.g., a cancer patient. In some embodiments, the cancer can be selected from a lung, ovarian, skin, uterine and esophageal cancer. In some embodiments, the cancer is lung squamous carcinoma, ovarian serous cystadenocarcinoma, skin cutaneous melanoma, uterine carcinosarcoma or esophageal carcinoma. In some embodiments, the fusion can be, e.g., a WASF2:FGR fusion. In some embodiments, the WASF2:FGR fusion has all or a part of the nucleotide sequence (such as, e.g., the fusion junction) set forth in SEQ ID NO:1.

In another aspect, the present disclosure provides a method of diagnosing a patient having a disease or disorder associated with aberrant FGR expression or activity, or overexpression of FGR; the method includes: (a) obtaining a biological sample from the patient; and (b) contacting the sample with a reagent that detects an FGR gene fusion to determine whether an FGR gene fusion is present in the biological sample, whereby the detection of the FGR gene fusion indicates the presence of a disorder associated with aberrant FGR expression or activity, or overexpression FGR.

The present disclosure also includes a method of determining a therapeutic regimen treating a cancer in a human subject; a method of identifying a patient likely to respond to treatment with an FGR inhibitor or an FGR fusion inhibitor; a method of stratifying a patient population by detecting an FGR fusion; a method of treating a patient; a method of inhibiting the proliferation of cells containing an FGR fusion; a method of reducing an activity of an FGR fusion; a method of treating a condition mediated by aberrant FGR expression or activity; a method of treating a condition characterized by overexpression of FGR; a method of identifying an agent that modulates the activity of an FGR fusion; and a method of monitoring disease burden in a patient having a condition mediated by FGR.

BRIEF DESCRIPTION OF THE FIGURES

FIG. 1 shows the nucleotide sequence of a WASF2:FGR gene fusion (SEQ ID NO:1) comprising exon number 1 of the WASF2 gene (Accession No. NM_006990) and exon numbers 2-13 of the FGR gene (Accession No. NM_005248). The slash after nucleotide 182 indicates the breakpoint (fusion junction) where the fusion has occurred. The underlined nucleotides are the start codon for FGR transcription.

DETAILED DESCRIPTION

The invention is based, at least in part, on the discovery of novel recombination or translocation events in cancer patients that result in at least a fragment of an FGR acne linked to a non-homologous promoter via a recombination or translocation event that may result in aberrant expression (e.g., in a location where the kinase is not typically expressed) or overexpression of FGR. Thus, a new patient population is identified, which is characterized by the presence of an FGR fusion, such as, e.g., a WASF2:FGR gene fusion. This new patient population suffers from or is susceptible to disorders mediated by aberrant FGR expression or activity, or overexpression of FGR, such as, e.g., a cancer. In another aspect of the invention, a new subtype of cancer is identified, which is characterized by the presence of the FGR fusions described herein. In some embodiments, the new patient population suffers from or is susceptible to a lung, ovarian, skin, uterine or esophageal cancer characterized by the presence of an FGR fusion. In some embodiments, the cancer is lung squamous carcinoma, ovarian serous cystadenocarcinoma, skin cutaneous melanoma, uterine carcinosarcoma or esophageal carcinoma. New methods of diagnosing and treating the patient population and the FGR fusion cancer subtype are also provided.

Figure 2:
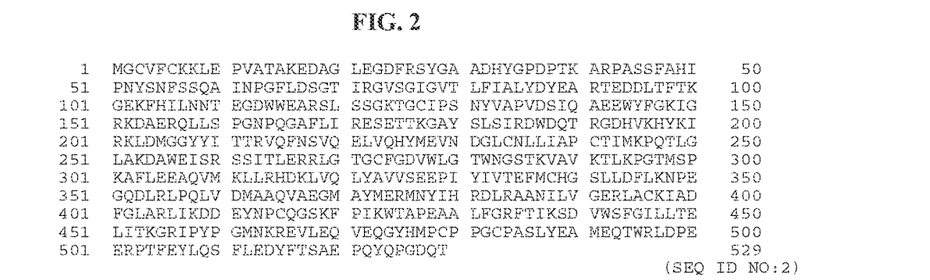
FIG. 2 shows the amino acid sequence for FGR (SEQ ID NO:2).
Figure 3A:
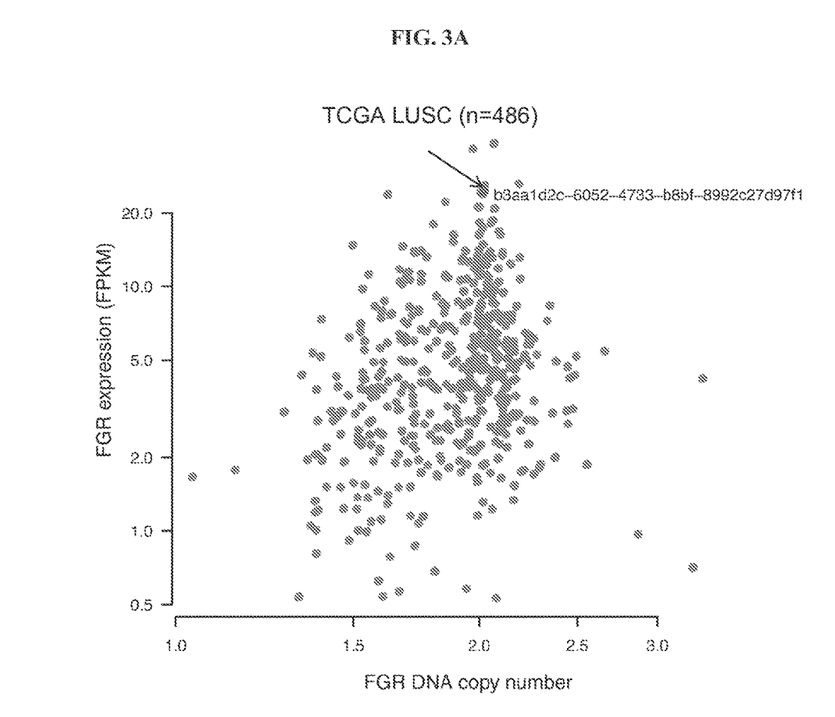
FIG. 3A is a graph showing FGR DNA copy number versus the mRNA expression in lung squamous carcinoma (LUSC) samples.
Figure 3B:
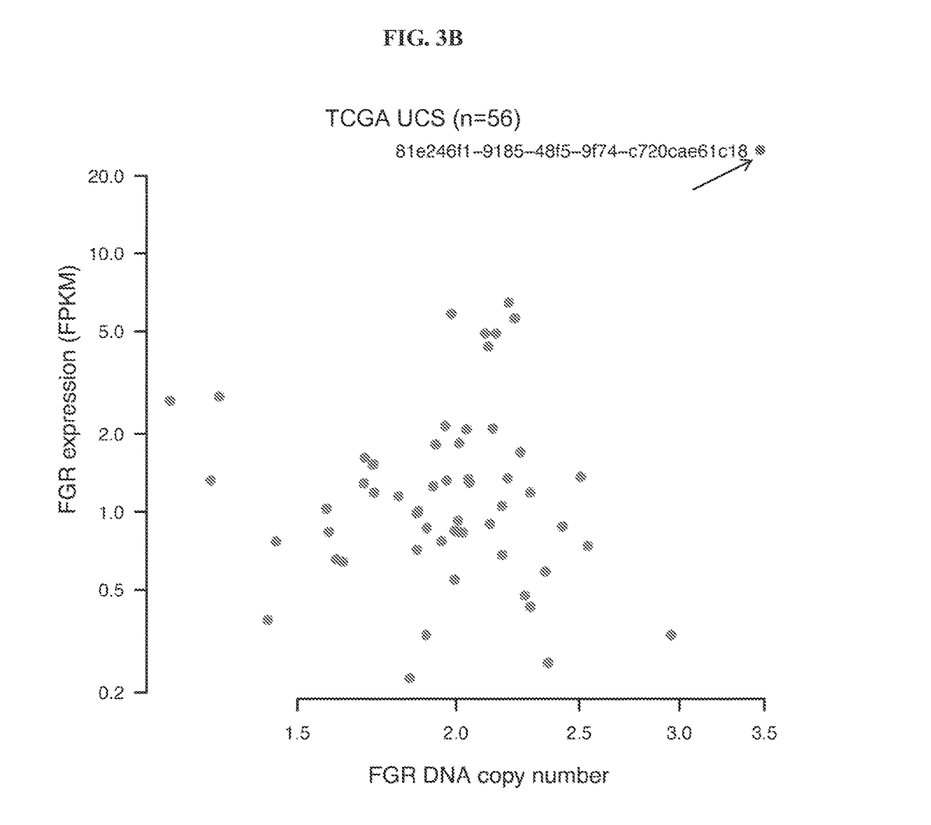
FIG. 3B is a graph showing FGR DNA copy number versus mRNA expression in uterine carcinosarcoma (UCS) samples.
Figure 3C:
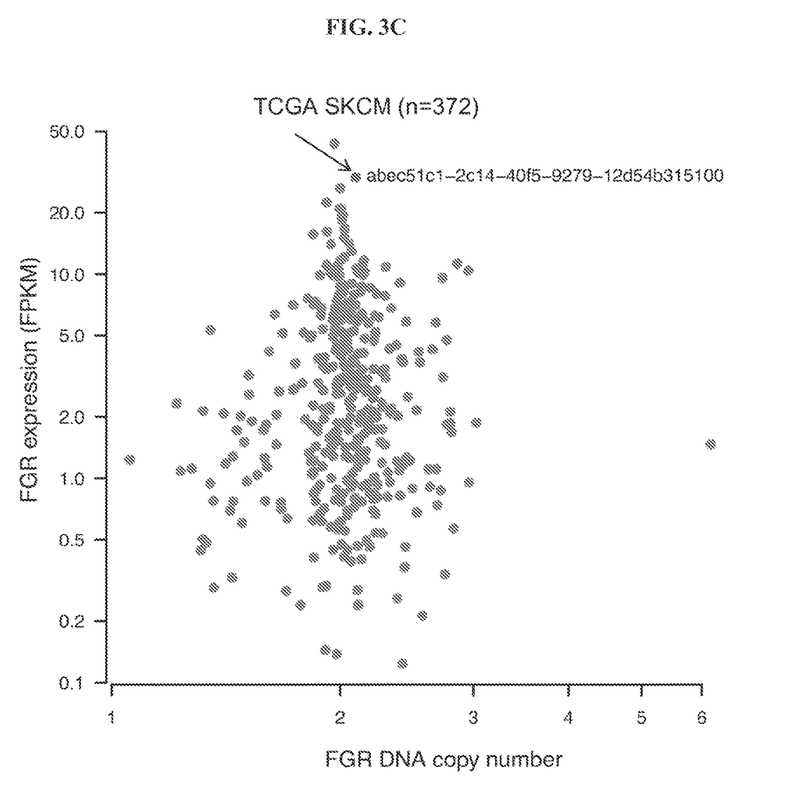
FIG. 3C is a graph showings FGR DNA copy number versus mRNA expression in skin cutaneous melanoma (SKCM) samples.
Figure 3D:
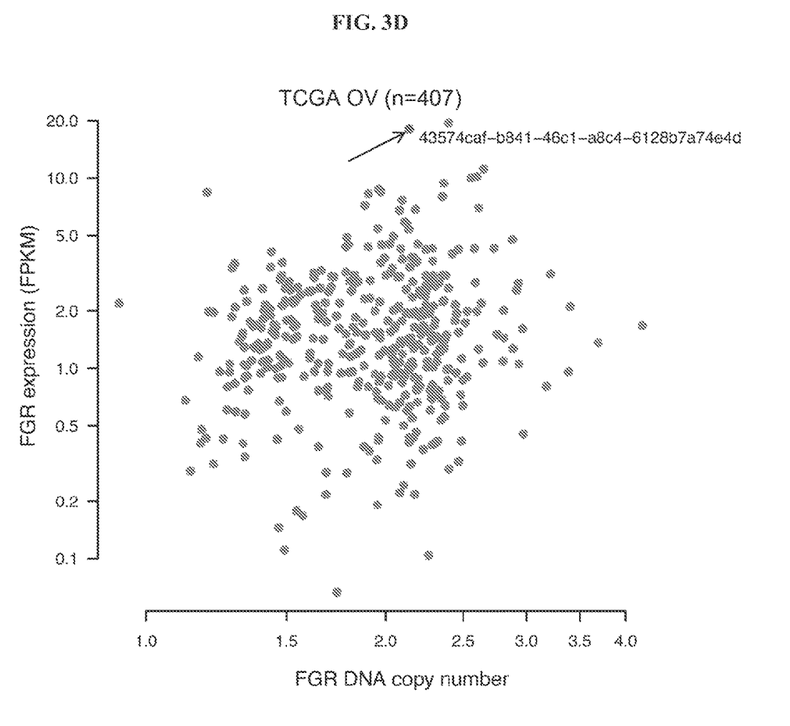
FIG. 3D is a graph showings FGR DNA copy number versus mRNA expression in ovarian serous cystadenocarcinoma (OV) samples.
Figure 3E:
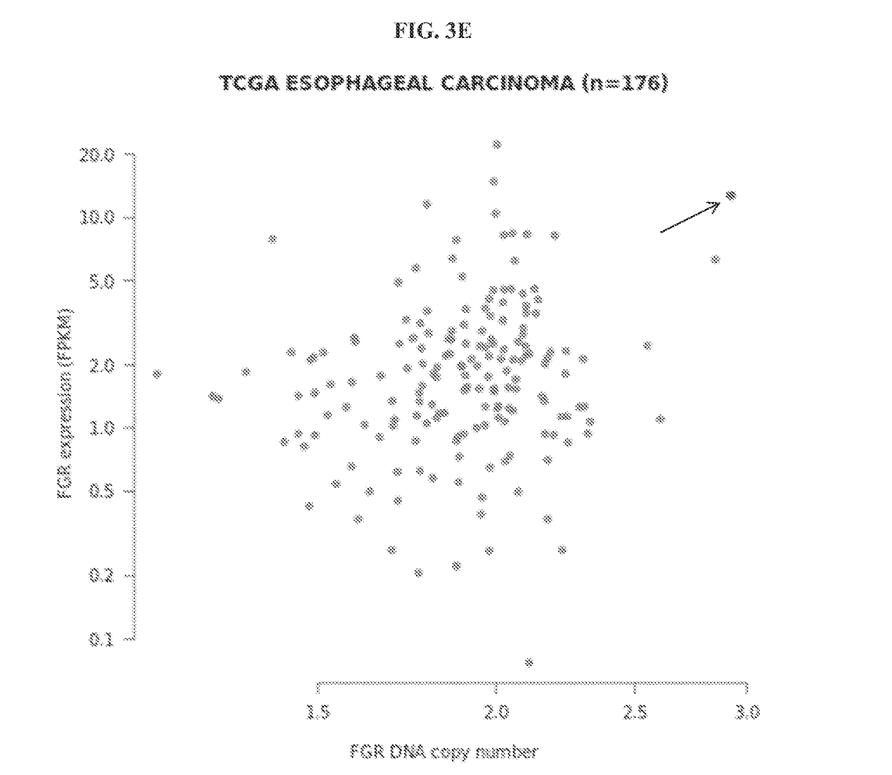
FIG. 3E is a graph showings FGR DNA copy number versus mRNA expression in esophageal carcinoma samples.

The feline Gardner-Rasheed sarcoma viral oncogene homolog (FGR) is a member of the Src family of protein tyrosine kinases (PTKs). FGR is a known proto-oncogene, and aberrant activity of FGR leads to a variety of disorders such as cancers. The encoded protein localizes to plasma membrane ruffles, and functions as a negative regulator of cell migration and adhesion triggered by the beta-2 integrin signal transduction pathway. FIGS. 3A-3E show the DNA copy number versus the mRNA expression (from TCGA) for lung squamous carcinoma (LUSC), uterine carcinosarcoma (UCS), skin cutaneous melanoma (SKCM), ovarian serous cystadenocarcinoma (OV) and esophageal carcinoma; the arrow shows the sample in which an FGR fusion has occurred. In each case, the fusions occur in samples with near-diploid FGR copy number, and FGR mRNA expression is among the highest of that cancer type. This is evidence that FGR fusions such as the ones described here lead to overexpression of FGR.

The term "FGR fusion" is used generically herein, and includes any fusion molecule (e.g., gene, gene product (e.g., cDNA, mRNA, or protein), and variants thereof) that includes a fragment from the FGR gene, particularly the coding region for the kinase domain of FGR, and a fragment from a second non-homologous gene, such that the coding sequence for the kinase domain of FGR is under control of the promoter of the non-homologous gene. FGR fusions can include, but not limited to, FGR gene fusions and FGR protein fusions. FGR and the gene that it is fused to are referred to as "fusion partners." Depending on where the fusion junction is, the fusion protein that is expressed may include at least the kinase domain of FGR. In some embodiments, the protein that is expressed includes the full FGR protein sequence.

FGR Gene Fusions

FGR gene fusions are generated by a fusion between at least a part of the FGR gene and a part of another gene as a result of a translocation (including inversion) within a chromosome or between chromosomes. As a result of a translocation, the FGR gene may be placed under the transcriptional control of the partner gene promoter, resulting in aberrant FGR expression or activity or overexpression of FGR. The FGR gene fusions disclosed herein can be associated with certain cancers, such as, e.g., lung cancer, ovarian cancer, skin cancer, uterine cancer or esophageal cancer. In some embodiments, the cancers associated with an FGR gene fusion is lung squamous carcinoma, ovarian serous cystadenocarcinoma, skin cutaneous melanoma, uterine carcinosarcoma or esophageal carcinoma. In some embodiments, the FGR gene fusions disclosed herein can be associated with other disorders mediated by aberrant FGR expression or activity, or overexpression of FGR.

Reference to "all or a portion" or "all or part" of an FGR gene fusion or SEQ ID NO:1, means that the nucleotide sequence comprises the entire FGR gene fusion nucleotide sequence or a fragment of that sequence that comprises the fusion junction or breakpoint between FGR and its fusion partner (such as, e.g., WASF2). The fragment may comprise 7, 8, 9, 10, 12, 14, 16, 18, 20, 21, 22, 23, 24, 25, 26, 27, 28, 29, 30, 35, 40, 45, 50, 60, 70, 80, 90, 100, 120, 150, 175, 200, 250, 300, or more nucleotides spanning the fusion junction of the FGR gene fusion.

In some exemplary embodiments, the fusion partner is all or a portion of WASF2 (Wiskott-Aldrich syndrome protein family, member 2). In one embodiment, a fusion includes an exon of the gene WASF2 (e.g., one or more exons encoding a WASF2 promoter or a functional fragment thereof) and an exon of the FGR gene (e.g., one or more exons encoding a kinase domain of FGR or a functional fragment thereof). Such a fusion can be referred to as a WASF2:FGR fusion. As used herein, the 5'-region is upstream of, and the 3'-region is downstream of, a fusion point in one of the component genes. In one embodiment, the WASF2:FGR fusion causes the FGR protein (e.g., a kinase domain of FGR, or a functional fragment thereof) to be over-expressed. In one embodiment, the WASF2:FGR fusion causes the full-length (wild type) FGR protein to be over-expressed.

In a particular embodiment, the present disclosure provides a WASF2:FGR gene fusion comprising the nucleotide sequence depicted in FIG. 1 (SEQ ID NO:1), or a fragment thereof that includes the fusion junction, SEQ ID NO:1 comprises WASF2 up to exon number 1, in the untranslated region of the WASF2 gene, fused to exon number 2 of FGR, in the untranslated region of the FGR gene. In some embodiments, the WASF2:FGR gene fusion codes for wild-type FGR protein (SEQ ID NO:2). In some embodiments, the WASF2:FGR gene fusion comprises a nucleotide sequence that is at least 85%, at least 90%, at least 95%, at least 97%, at least 98%, or at least 99% identical to all or part of SEQ ID NO:1.

The nucleic acid sequences of FGR gene fusions may be used as probes, primers, or bait to identify nucleotides from a biological sample that include, flank, or hybridize to FGR fusions, such as WASF2:FGR (e.g., all or part of SEQ ID NO: 1), at, e.g., the fusion junction. In certain embodiments, the probe, primer, or bait molecule is an oligonucleotide that allows capture, detection, and/or isolation of an FGR gene fusion in a sample. In certain embodiments, the probes or primers derived from the nucleic acid sequences of FGR gene fusions (e.g., from the fusion junctions) may be used, for example, for polymerase chain reaction (PCR) amplification. The oligonucleotide can comprise a nucleotide sequence substantially complementary to a fragment of the FGR gene fusion nucleic acid molecules described herein. The sequence identity between the nucleic acid fragment, e.g., the oligonucleotide and the target FGR gene fusion sequence, need not be exact, so long as the sequences are sufficiently complementary to allow the capture, detection, and/or isolation of the target sequence. In one embodiment, the nucleic acid fragment is a probe or primer that includes an oligonucleotide between about 5 and 25, e.g., between 10 and 20, or between 10 and 15, nucleotides in length that includes the fusion junction of an FGR fusion, such as e.g., WASF2:FGR (e.g., all or part of SEQ ID NO: 1). In other embodiments, the nucleic acid fragment is a bait that includes an oligonucleotide between about 100 to 300 nucleotides, 130 and 230 nucleotides, or 150 and 200 nucleotides in length that includes the fusion junction of an FGR fusion, such as e.g., WASF2:FGR (e.g., all or part of SEQ ID NO: 1).

In certain embodiments, the nucleic acid fragments hybridize to a nucleotide sequence that includes a breakpoint or fusion junction, e.g., a breakpoint or fusion junction as identified by a slash ("/") in FIG. 1. For example, the nucleic acid fragment can hybridize to a nucleotide sequence that includes the fusion junction between the WASF2 transcript and the FGR transcript, i.e., a nucleotide sequence that includes a portion of SEQ ID NO: 1 (e.g., nucleotides 181-184 of SEQ NO:1). In some embodiments, the nucleic acid fragment includes a nucleotide sequence within exon 1 of a WASF2 gene and exons 2-13 of an FGR gene (e.g., a portion of SEQ ID NO: 1 comprising nucleotides 181-184, such as, e.g., a sequence comprising nucleotides 178-187, 173-192, 158-207, 133-232, 108-257, or 83-282 of SEQ ID NO: 1).

In other embodiments, the nucleic acid fragment includes a bait that comprises a nucleotide sequence that hybridizes to an FGR gene fusion nucleic acid molecule described herein, and thereby allows the detection, capture, and/or isolation of the nucleic acid molecule. In one embodiment, a bait is suitable for solution phase hybridization. In other embodiments, a bait includes a binding entity or detection entity, e.g., an affinity tag or fluorescent label, that allows detection, capture, and/or separation, e.g., by binding to a binding entity, of a hybrid formed by a bait and a nucleic acid hybridized to the bait. In exemplary embodiments, the nucleic acid fragments used as bait comprise a nucleotide sequence within SEQ ID NO:1 comprising nucleotides 181-184 (such as, e.g., a sequence comprising nucleotides 178-187, 173-192, 158-207, 133-232, 108-257, or 83-282 of SEQ ID NO:1).

Detection and Diagnostic Methods

In another aspect, the present disclosure provides a method of detecting the presence of an FGR gene fusion, such as, e.g., a WASF2:FGR fusion as described herein. The presence of an FGR fusion can indicate that the mammal providing the biological sample suffers from or is at risk of developing a disorder mediated by aberrant FGR expression or activity, or overexpression of FGR, such as, e.g., a cancer. The presence of an FGR gene fusion may also indicate that the cancer is treatable with an FGR inhibitor (such as, e.g., a kinase inhibitor or an antibody specific to FGR) or an FGR fusion inhibitor. In some embodiments, the FGR fusion present in the sample is WASF2:FGR and the cancer to be treated is selected from a lung, ovarian, skin, uterine cancer and esophageal cancer. In some embodiments, the cancer is lung squamous carcinoma, ovarian serous cystadenocarcinoma, skin cutaneous melanoma, uterine carcinosarcoma or esophageal carcinoma.

In one embodiment, the FGR fusion detected is a nucleic acid molecule. The method includes detecting whether an FGR fusion nucleic acid molecule is present in a cell (e.g., a circulating cell or a cancer cell), a tissue (e.g., a tumor), or a sample, e.g., a tumor sample, from a subject. In one embodiment, the sample is a nucleic acid sample. In one embodiment, the nucleic acid sample comprises DNA, e.g., genomic DNA or cDNA, or RNA, e.g., mRNA. In some embodiments, the sample is from a mammalian (e.g., human) cancer. In some embodiments, the human cancer is selected from a lung, ovarian, skin, uterine cancer and esophageal cancer. In some embodiments, the human cancer is lung squamous carcinoma, ovarian serous cystadenocarcinoma, skin cutaneous melanoma, uterine carcinosarcoma or esophageal carcinoma.

The methods described herein may be employed to detect the presence of an FGR fusion polynucleotide in a biological sample of a mammal. One such method comprises the steps of obtaining a biological sample from the mammal and contacting that sample with at least one reagent that detects an FGR fusion, to determine whether an FGR fusion is present in the biological sample. The sample can be chosen from one or more of sample types, such as, for example, tissue, e.g., cancerous tissue (e.g., a tissue biopsy), whole blood, serum, plasma, buccal scrape, sputum, saliva, cerebrospinal fluid, urine, stool, circulating tumor cells, circulating nucleic acids, or bone marrow.

In some embodiments, the FGR fusion is detected in a nucleic acid molecule by one or more methods chosen front: nucleic acid hybridization assays (e.g. in situ hybridization, comparative genomic hybridization, microarray, Southern blot, northern blot), amplification-based assays (e.g., PCR, PCR-RFLP assay, or real-time PCR), sequencing and genotyping (e.g. sequence-specific primers, high-performance liquid chromatography, or mass-spectrometric genotyping), and screening analysis (including metaphase cytogenetic analysis by karyotype methods).

(1) Hybridization Methods

In some embodiments, the reagent hybridizes to an FGR gene fusion. In some embodiments, the reagent hybridizes to a nucleotide sequence that includes the fusion junction of an FGR gene fusion, such as, e.g., nucleotides 178-187, 173-192, 173-192, 158-207, 133-232, 108-257, or 83-282 of SEC) ID NO:1.

In one embodiment, the method includes: contacting a nucleic acid sample, e.g., a genomic DNA sample (e.g., a chromosomal sample or a fractionated, enriched or otherwise pre-treated sample) or a gene product (e.g., mRNA, or cDNA), obtained from the subject, with a nucleic acid fragment, e.g., a probe or primer as described herein (e.g., an exon-specific or a breakpoint-specific probe or primer), under conditions suitable for hybridization, and determining the presence or absence of the FGR gene fusion, such as, e.g., WASF2:FGR as described herein.

Hybridization, as described throughout the specification, may be carried out under stringent conditions, e.g., medium or high stringency. See, e.g., J. Sambrook, E. F. Fritsch, and T. Maniatis, *Molecular Cloning: A Laboratory Manual*, Cold Spring Harbor Laboratory Pr; 2nd edition (1989); T. Brown, *Hybridization Analysis of DNA Blots. Current Protocols in Molecular Biology* at 21:2.10.1-2:10.16 (2001). High stringency conditions for hybridization refer to conditions under which two nucleic acids must possess a high degree of base pair homology to each other in order to hybridize. Examples of highly stringent conditions for hybridization include hybridization in 4×sodium chloride/sodium citrate (SSC), at 65 or 70° C., or hybridization in 4×SSC plus 50% formamide at about 42 or 50° C., followed by at least one, at least two, or at least three washes in 1×SSC, at 65 or 70° C. Another example of highly stringent conditions includes hybridization in 2×SSC; 10×Denhardt solution (Fikoll 400+PEG+BSA; ratio 1:1:1); 0.1% SDS; 5 mM EDTA; 50 mM $Na_2HPO_4$; 250 μg/ml of herring sperm DNA; 50 μg/ml of tRNA; or 0.25 M of sodium phosphate buffer, pH 7.2; 1 mM EDTA7% SDS at 60° C.; followed by washing 2×SSC, 0.1% SDS at 60° C.

The nucleic acid fragments can be detectably labeled with, e.g., a radiolabel, fluorescent label, a bioluminescent label, a chemiluminescent label, an enzyme label, a binding pair label (e.g., biotin/streptavidin), an antigen label, or can include an affinity lag, or identifier (e.g., an adaptor, barcode or other sequence identifier). Labeled or unlabeled nucleic acids and/or nucleic acid fragments may be used in reagents for detecting, capturing, or isolating FGR gene fusions. Labeled or unlabeled nucleic acids and/or nucleic acid fragments may be used in reagents for detecting, capturing, and/or isolating FGR gene fusions, such as, e.g., WASF2: FGR (e.g., all or part of SEQ ID NO: 1). In some embodiments, the labeled reagent can be detected using, e.g., autoradiography, microscopy (e.g., brightfield, fluorescence, or electron microscopy), enzyme-linked immunosorbent assay (ELISA), or immunohistochemistry.

In some embodiments, the method comprises performing chromosome in situ hybridization with chromosomal DNA from a biological sample to detect the presence of an FGR gene fusion (such as, e.g., WASF2:FGR, as disclosed herein). In some embodiments, the chromosome in situ hybridization comprises the steps of: providing a chromosome (e.g., interphase or metaphase chromosome) preparation (e.g., by attaching the chromosomes to a substrate (e.g., glass)); denaturing the chromosomal DNA (e.g., by exposure to formamide) to separate the double strands of the polynucleotides from each other; exposing the nucleic acid probe to the chromosomes under conditions to allow hybridization of the probe to the target DNA; removing unhybridized or non-specifically hybridized probes by washing; and detecting the hybridization of the probe with the target DNA. In some embodiments, the chromosome in situ hybridization is fluorescence in situ hybridization (FISH). In some embodiments, the probe is labeled directly by a fluorescent label, or indirectly by incorporation of a nucleotide containing a tag or reporter molecule (e.g., biotin, digoxigenin, or hapten) which after hybridization to the target DNA is then bound by fluorescently labeled affinity molecule (e.g., an antibody or streptavidin). In some embodiments, the hybridization of the probe with the target DNA in FISH can be visualized using a fluorescence microscope.

In other embodiments, the method comprises performing Southern blot with DNA polynucleotides from a biological sample to detect the presence of an FGR gene fusion (such as, e.g., WASF2:FGR, as disclosed herein). In some embodiments, the Southern blot comprises the steps of: optionally fragmenting the polynucleotides into smaller sizes by restriction endonucleases; separating the polynucleotides by gel electrophoresis; denaturing the polynucleotides (e.g., by heat or alkali treatment) to separate the double strands of the polynucleotides from each other; transferring the polynucleotides from the gel to a membrane (e.g., a nylon or nitrocellulose membrane); immobilizing the polynucleotides to the membrane (e.g., by UV light or heat); exposing the nucleic acid probe to the polynucleotides under conditions to allow hybridization of the probe to the target DNA; removing unhybridized or non-specifically hybridized probes by washing; and detecting the hybridization of the probe with the target DNA.

(2) Amplification-Based Assays

In certain embodiments, the method of determining the presence of an FGR gene fusion, comprises (a) performing a PCR amplification reaction with polynucleotides from a biological sample, wherein the amplification reaction utilizes a pair of primers which will amplify at least a fragment of the FGR gene fusion, wherein the fragment comprises the fusion junction, wherein the first primer is in sense orientation and the second primer is in antisense orientation; and (b) detecting an amplification product, wherein the presence of the amplification product is indicative of the presence of an FGR fusion poly nucleotide in the sample. In specific exemplary embodiments, the FGR gene fusion is WASF2: FGR, such as, e.g., the gene fusion of SEQ ID NO: 1, or a fragment thereof comprising nucleotides 181-184, 178-187, 173-192, 158-207, 133-232, 108-257, or 83-282 of SEQ ID NO:1.

In some embodiments, step (a) of performing a PCR amplification reaction comprises: (i) providing a reaction mixture comprising the polynucleotides (e.g., DNA or cDNA) from the biological sample, the pair of primers which will amplify at least a fragment of the FGR gene fusion wherein the first primer is complementary to a sequence on the first strand of the polynucleotides and the second primer is complementary to a sequence on the second strand of the polynucleotides, a DNA polymerase, and a plurality of free nucleotides comprising adenine, thymine, cytosine, and guanine (dNTPs); (ii) heating the reaction mixture to a first predetermined temperature for a first predetermined time to separate the double strands of the polynucleotides from each other; (iii) cooling the reaction mixture to a second predetermined temperature for a second predetermined time under conditions to allow the first and second primers to hybridize with their complementary sequences on the first and second strands of the polynucleotides, and to allow the DNA polymerase to extend the primers; and (iv) repeating steps (ii) and (iii) for a predetermined number of cycles (e.g., 10, 15, 20, 25, 30, 35, 40, 45, or 50 cycles).

In some embodiments, the polynucleotides from the biological sample comprise RNA, and the method further comprises performing a RT-PCR amplification reaction with the RNA to synthesize cDNA as the template for subsequent or simultaneous PCR reactions. In some embodiments, the RT-PCR amplification reaction comprises providing a reaction mixture comprising the RNA, a primer which will amplify the RNA (e.g., a sequence-specific primer, a random primer, or oligo(dT)s), a reverse transcriptase, and dNTPs, and heating the reaction mixture to a third predetermined temperature for a third predetermined time under conditions to allow the reverse transcriptase to extend the primer.

(3) Sequencing and Genotyping

Another method for determining the presence of an FGR gene fusion molecule (such as, e.g., WASF2:FGR, as disclosed herein) includes: sequencing a portion of the nucleic acid molecule (e.g., sequencing the portion of the nucleic acid molecule that comprises the fusion junction of an FGR gene fusion), thereby determining that the FGR gene fusion is present in the nucleic acid molecule. Optionally, the sequence acquired is compared to a reference sequence, or a wild type reference sequence. In one embodiment, the sequence is determined by a next generation sequencing method. In some embodiments, the sequencing is automated and/or high-throughput sequencing. The method can further include acquiring, e.g., directly or indirectly acquiring, a sample, e.g., a tumor or cancer sample, from a patient.

In some embodiments, the sequencing comprises chain terminator sequencing (Sanger sequencing), comprising: providing a reaction mixture comprising a nucleic acid molecule from a biological sample, a primer complementary to a region of the template nucleic acid molecule, a DNA polymerase, a plurality of free nucleotides comprising adenine, thymine, cytosine, and guanine (dNTPs), and at least one chain terminating nucleotide (e.g., at least one di-deoxynucleotide (ddNTPs) chosen from ddATP, ddTTP, ddCTP, and ddGTP), wherein the at least one chain terminating nucleotide is present in a low concentration so that chain termination occurs randomly at any one of the positions containing the corresponding base on the DNA strand; annealing the primer to a single strand of the nucleic acid molecule; extending the primer to allow incorporation of the chain terminating nucleotide by the DNA polymerase to produce a series of DNA fragments that are terminated at positions where that particular nucleotide is used; separating the polynucleotides by electrophoresis (e.g., gel or capillary electrophoresis); and determining the nucleotide order of the template nucleic acid molecule based on the positions of chain termination on the DNA fragments. In some embodiments, the sequencing is carried out with four separate base-specific reactions, wherein the primer or the chain terminating nucleotide in each reaction is labeled with a separate fluorescent label. In other embodiments, the sequencing is carried out in a single reaction, wherein the four chain terminating nucleotides mixed in the single reaction are each labeled with a separate fluorescent label.

In some embodiments, the sequencing comprises pyrosequencing (sequencing by synthesis), comprising: (i) providing a reaction mixture comprising a nucleic acid molecule from a biological sample, a primer complementary to a region of the template nucleic acid molecule, a DNA polymerase, a first enzyme capable of converting pyrophosphate into ATP, and a second enzyme capable using ATP to generates a detectable signal (e.g., a chemiluminescent signal, such as light) in an amount that is proportional to the amount of ATP; (ii) annealing the primer to a single strand of the nucleic acid molecule; (iii) adding one of the four free nucleotides (dNTPs) to allow incorporation of the correct, complementary dNTP onto the template by the DNA polymerase and release of pyrophosphate stoichiometrically; (iv) convening the released pyrophosphate to ATP by the first enzyme; (v) generating a detectable signal by the second enzyme using the ATP; (vi) detecting the generated signal and analyzing the amount of signal generated in a pyrogram; (vii) removing the unincorporated nucleotides; and (viii) repeating steps (iii) to (vii). The method allows sequencing of a single strand of DNA, one base pair at a time, and detecting which base was actually added at each step. The solutions of each type of nucleotides are sequentially added and removed from the reaction. Light is produced only when the nucleotide solution complements the first unpaired base of the template. The order of solutions which produce detectable signals allows the determination of the sequence of the template.

In some embodiments, the method of determining the presence of an FGR fusion (such as, e.g., WASF2:FGR, as disclosed herein) comprises analyzing a nucleic acid sample (e.g., DNA, cDNA, or RNA, or an amplification product thereof) by HPLC. The method tray comprise: passing a pressurized liquid solution containing the sample through a column filled with a sorbent, wherein the nucleic acid or protein components in the sample interact differently with the sorbent, causing different flow rates for the different components; separating the components as they flow out the column at different flow rates. In some embodiments, the HPLC is chosen from, e.g., reverse-phase HPLC, size exclusion HPLC, ion-exchange HPLC, and bioaffinity HPLC.

In some embodiments, the method of determining the presence of an FGR fusion (such as, e.g., WASF2:FGR, as disclosed herein) comprises analyzing a nucleic acid sample (e.g., DNA, cDNA, or RNA, or an amplification product thereof) by mass spectrometry. The method may comprise: ionizing the components in the sample (e.g., by chemical or electron ionization); accelerating and subjecting the ionized components to an electric or magnetic field; separating the ionized components based on their mass-to-charge ratios; and detecting the separated components by a detector capable of detecting charged particles (e.g., by an electron multiplier).

Detection of an FGR gene fusion in a patient can lead to assignment of the patient to the newly identified patient population that bears the FGR gene fusion. Because this patient population can suffer from or be susceptible to a disorder associated with aberrant FGR expression or activity, or overexpression of FGR, detection of an FGR gene fusion can also lead to diagnosis of such disorder. Thus, a further aspect of the present disclosure provides a method of stratifying a patient population (e.g., assigning a patient, to a group or class) and/or diagnosing a patient, comprising: obtaining a biological sample from the patient, contacting the sample with at least one reagent that detects an FGR gene fusion to determine whether an FGR fusion is present in the biological sample. The detection of an FGR fusion indicates that the patient belongs to the newly identified patient population that bears the FGR gene fusion, and/or the presence of a disorder associated with aberrant FGR expression or activity or overexpression of FGR, such as e.g., a cancer. The detection of an FGR fusion also identifies a new subtype of cancer, which is characterized by the presence of the FGR fusion. In some embodiments, the cancer is lung cancer, ovarian cancer, skin cancer, uterine cancer or esophageal cancer. In some embodiments, the cancer is chosen from, e.g., lung squamous carcinoma, ovarian serous cystadenocarcinoma, skin cutaneous melanoma, uterine carcinosarcoma and esophageal carcinoma. In certain embodiments, the FGR fusion is WASF2:FGR. In some embodiments, the WASF2:FGR fusion has all or a part of the nucleotide sequence (such as, e.g., the fusion junction) set forth in SEQ ID NO:1.

In some embodiments, the FGR gene fusion is detected prior to initiating, during, or after, a treatment of a patient with, e.g., an FGR inhibitor or an FGR fusion inhibitor. In one embodiment, the FGR gene fusion is detected at the time the patient is diagnosed with a disorder, e.g., a cancer. In other embodiment, the FGR fusion is detected at a predetermined interval, e.g., a first point in time and at least at a subsequent point in time. In certain embodiments, in response to detection of an FGR fusion, such as, e.g., WASF2:FGR, the method further includes one or more of:

(1) stratifying a patient population (e.g., assigning a patient, to a group or class);
(2) identifying; or selecting the patient as likely or unlikely to respond to a treatment, e.g., an FGR inhibitor treatment (e.g., a kinase inhibitor treatment) or an FGR fusion inhibitor treatment as described herein;
(3) selecting a treatment regimen, e.g., administering or not administering a preselected therapeutic agent, such as, e.g., an FGR inhibitor or an FGR fusion inhibitor;
(4) prognosticating the time course of the disease in the patient (e.g., evaluating the likelihood of increased or decreased patient survival); or
(5) monitoring the effectiveness of treatment (e.g., by detecting a reduction in the level of FGR fusion in a patient sample).

In certain embodiments, upon detection of an FGR gene fusion in a patient's biological sample, the patient is identified as likely to respond to a treatment that comprises an FGR inhibitor or an FGR fusion inhibitor. In some embodiments, the FGR fusion detected is a WASF2:FGR fusion.

A further aspect of the present disclosure provides a method of selecting a treatment option by detecting an FGR fusion. The method comprises obtaining a biological sample from a patient and exposing the sample to at least one reagent that detects an FGR gene fusion to determine whether an FGR fusion is present in the biological sample. The detection of the FGR gene fusion indicates the likelihood of the patient responding to treatment with an FGR inhibitor or an FGR fusion inhibitor. The method may be augmented or personalized by evaluating the effect of a variety of FGR inhibitors or FGR fusion inhibitors on the biological sample shown to contain an FGR fusion to determine the most appropriate inhibitor to administer. In certain embodiments, the FGR fusion is WASF2:FGR. In some embodiments, the WASF2:FGR fusion has all or a part of the nucleotide sequence (such as, e.g., the fusion junction) set forth in SEQ ID NO:1.

Methods of Treatment

Alternatively, or in combination with the detection and diagnostic methods described herein, the present disclosure provides methods for treating the newly identified patient population and the new FGR fusion cancer subtype, which are characterized by the presence of an FGR fusion. The patient population and cancer subtype can be associated with or predict the onset of a condition mediated by aberrant FGR expression or activity, or overexpression of FGR, such as, e.g., a cancer or a tumor harboring an FGR fusion. The methods comprise administering a therapeutic agent, e.g., an FGR inhibitor, such as e.g., a kinase inhibitor or an antibody specific to FGR, or an FGR fusion inhibitor, such as, e.g., an RNA inhibitor that recognizes FGR or the fusion junction of an FGR gene fusion, including but not limited to siRNA, dsRNA, shRNA, or any other antisense nucleic acid inhibitor, as described herein, alone or in combination with e.g., other chemotherapeutic agents or procedures, in an amount sufficient to treat a condition mediated by aberrant FGR expression or activity, or overexpression of FGR, by one or more of the following: e.g., impeding growth of a cancer, causing a cancer to shrink by weight or volume, extending the expected survival time of the patient, inhibiting tumor growth, reducing tumor mass, reducing size or number of metastatic lesions, inhibiting the development of new metastatic lesions, prolonging survival, prolonging progression-free survival, prolonging time to progression, and/or enhancing quality of life.

In certain embodiments, the FGR fusion of the invention may be inhibited by an FGR inhibitor or an FGR fusion inhibitor. In some embodiments, the therapeutic agent is an FGR inhibitor, such as, e.g., a compound, biological or chemical, which inhibits, directly or indirectly, the expression and/or activity of FGR. For example, the FGR inhibitors may be an antibody (such as, e.g., an anti-FGR antibody) or a small molecule inhibitor (such as, e.g., a kinase inhibitor). In some embodiments, the inhibitors may act directly on FGR itself, modify the activity of FGR, or inhibit the expression of FGR. In other embodiments, the inhibitors may indirectly inhibit FGR activity by inhibiting the activity of proteins or molecules other than FGR itself. For example, the inhibitors may modulate the activity of regulatory kinases that phosphorylate or dephosphorylate FGR, interfere with binding of ligands, or inhibit the activity of interacting or downstream proteins or molecules.

In other embodiments, the therapeutic agent is an FGR fusion inhibitor that inhibits the expression of nucleic acid encoding an FGR fusion. Examples of FGR fusion inhibitors include nucleic acid molecules, for example, antisense molecules, ribozymes, RNAi, or triple helix molecules, that hybridize to a nucleic acid encoding an FGR fusion (e.g., genomic DNA, or mRNA), or a transcription and/or translation regulatory region, and blocks or reduces mRNA and/or protein expression of an FGR fusion. In some embodiments, the antisense molecule recognizes the WASF2:FGR fusion junction, or an RNA inhibitor, including but not limited to small interfering RNA (siRNA), double stranded RNA (dsRNA), and short-hairpin RNA (shRNA), or any other antisense nucleic acid inhibitor, specific to the WASF2:FGR fusion junction.

As used herein, and unless otherwise specified, a "therapeutically effective amount" of a compound is an amount sufficient to provide a therapeutic benefit in the treatment or Management of a condition mediated by aberrant FGR expression or activity, or overexpression of FGR, such as, delaying or minimizing one or more symptoms associated with a cancer or a tumor harboring an FGR fusion (such as, e.g., WASF2:FGR, as described herein). A therapeutically effective amount of a compound means an amount of therapeutic agent, alone or in combination with other therapeutic agents, which provides a therapeutic benefit in the treatment or management of the condition. The term "therapeutically effective amount" can encompass an amount that improves overall therapy, reduces or avoids symptoms or causes of the condition mediated by aberrant FGR expression or activity or overexpression of FGR, or enhances the therapeutic efficacy of another therapeutic agent.

In certain embodiments, the cancer or tumor harboring an FGR fusion is lung cancer, ovarian cancer, skin cancer, uterine cancer or esophageal cancer. In some embodiments, the cancer or tumor harboring an FGR fusion is chosen from, e.g., lung squamous carcinoma, ovarian serous cystadenocarcinoma, skin cutaneous melanoma, uterine carcinosarcoma, and esophageal carcinoma.

In some embodiments, the patient to be treated is suffering from a condition mediated by aberrant FGR expression or activity, or overexpression of FGR, e.g., cancer or a tumor harboring an FGR fusion (such as, e.g., lung squamous carcinoma, ovarian serous cystadenocarcinoma, skin cutaneous melanoma, uterine carcinosarcoma or esophageal carcinoma). The method for treating the condition comprises administering to the patient a therapeutically effective amount of an FGR inhibitor or an FGR fusion inhibitor as described above.

Screening Methods

Therapeutic agents, such as e.g., FGR inhibitors or FGR fusion inhibitors, used in the therapeutic methods of the present disclosure can be evaluated using the screening assays described herein. Thus, the present disclosure provides a method of identifying an agent useful for treating a condition mediated by aberrant FGR expression or activity, overexpression of FGR, e.g., cancer or a tumor harboring an FGR fusion, which in some embodiments is selected from a lung, ovarian, skin, uterine cancer and esophageal cancer (such as e.g., lung squamous carcinoma, ovarian serous cystadenocarcinoma, skin cutaneous melanoma, uterine carcinosarcoma or esophageal carcinoma), comprising contacting a cell expressing an FGR gene fusion with a candidate agent and using the methods described herein to determine whether the expression level of the fusion is decreased or a biological function associated with the fusion is altered. In one embodiment, therapeutic agents can be evaluated in a cell-free system, e.g., a cell lysate or in a reconstituted system. In other embodiments, the therapeutic agents are evaluated in a cell in culture, e.g., a cell expressing an FGR fusion (e.g., a mammalian cell, a tumor cell or cell line, a recombinant cell). In yet other embodiments, the therapeutic agents are evaluated in a cell in vivo, e.g., an FGR fusion-expressing cell present in a subject, e.g., an animal subject (e.g., an in vivo animal model).

Exemplary parameters to evaluate in determining the efficacy of a therapeutic agent for treating a condition mediated by aberrant FGR expression or activity, or overexpression of FGR, such as, e.g., a cancer or a tumor harboring an FGR fusion, include one or more of:
(i) a change in an activity of a cell containing an FGR fusion (e.g., a tumor cell or a recombinant cell), e.g., a change in proliferation, morphology, migration, adhesion, or tumorigenicity of the cell;
(ii) a change in tumor present in an animal subject e.g., size, appearance, proliferation, or metastasis of the tumor;
(iii) a change in the level, e.g., expression level (transcription and/or translation) of an FGR gene fusion; or
(iv) a change in an activity of a signaling pathway involving FGR (e.g., the beta-2 integrin signaling pathway), e.g., phosphorylation or activity of an interacting or downstream protein, or expression of a downstream gene.

In some embodiments, the FGR fusion is a WASF2:FGR fusion.

In other embodiments, a change in an activity of a cell expressing an FGR fusion, such as, e.g., WASF2:FGR, as described herein, (e.g., a mammalian cell, a tumor cell or cell line, a recombinant cell) is detected in a cell in culture. In one embodiment, the cell is a recombinant cell that is modified to express an FGR fusion nucleic acid, e.g., is a recombinant cell transfected with an FGR fusion nucleic acid. The transfected cell can show a change in response to the expressed FGR fusion, e.g., increased proliferation, increased migration, decreased adhesion, changes in morphology, increased tumorigenicity, and/or acquired a transformed phenotype. A change in any of the activities of the cell, e.g., the recombinant cell, in the presence of the candidate agent can be detected. For example, a decrease in one or more of: e.g., proliferation, migration, tumorigenicity, transformed morphology, in the presence of the candidate agent can be indicative of an inhibitor of an FGR fusion. In other embodiments, a change in binding activity or phosphorylation of FGR or its interacting or downstream proteins or molecules as described herein is detected.

In yet other embodiment, a change in a tumor present in an animal subject (e.g., an in vivo animal model) is detected. In one embodiment, a tumor containing animal or a xenograft comprising cells expressing an FGR fusion (e.g., tumorigenic cells expressing an FGR fusion) is employed. The therapeutic agents can be administered to the animal subject and a change in the tumor is evaluated. In one embodiment, the change in the tumor includes one or more of, e.g., tumor growth, tumor size, tumor burden, tumor metastasis, or survival is evaluated. A decrease in one or more of tumor growth, tumor size, tumor burden, or tumor metastasis, or an increased survival is indicative that the candidate agent is an inhibitor.

Another aspect of the present disclosure provides a method or assay for screening for agents that modulate (e.g., inhibit) the expression or activity of an FGR fusion as described herein. The method includes contacting e.g., an FGR fusion, or a cell expressing an FGR fusion, with a candidate agent; and detecting a change in a parameter associated with an FGR fusion, e.g., a change in the expression or an activity of the FGR fusion. The method can, optionally, include comparing the treated parameter to a reference value, e.g., a control sample (e.g., comparing a parameter obtained from a sample with the candidate agent to a parameter obtained from a sample without the candidate agent). In one embodiment, if a decrease in expression or activity of the FGR fusion is detected, the candidate agent is identified as an inhibitor. In another embodiment, if an increase in expression or activity of the FGR fusion is detected, the candidate agent is identified as an activator. In certain embodiments, the fusion is an FGR gene fusion, e.g., a WASF2:FGR fusion.

In one embodiment, the contacting step is detected in a cell-free system, e.g., a cell lysate or in a reconstituted system. In other embodiments, the contacting step is detected in a cell in culture, e.g., a cell expressing an FGR fusion (e.g., a mammalian cell, a tumor cell or cell line, a recombinant cell). In yet other embodiments, the contacting step is detected in a cell in vivo, e.g., an FGR expressing cell present in a subject, e.g., an animal subject (e.g., an in vivo animal model).

Exemplary parameters evaluated in identifying an agent that modulates the activity an FGR fusion (e.g., a WASF2:FGR fusion) include one or more of:
(i) a change in an activity of a cell containing an FGR fusion (e.g., a tumor cell or a recombinant cell), e.g., a change in proliferation, morphology, migration, adhesion, or tumorigenicity of the cell;
(ii) a change in tumor present in an animal subject, size, appearance, proliferation, or metastasis of the tumor;
(iii) a change in the level, e.g., expression level (transcription and/or translation) of an FGR fusion; or
(iv) a change in an activity of a signaling pathway involving FGR (e.g., the beta-2 integrin signaling pathway), e.g., phosphorylation or activity of an interacting downstream protein, or expression of a downstream gene.

Methods for Validating FGR Fusions

FGR gene fusions (such as, e.g., WASF2:FGR gene fusion) may be evaluated to ensure that the breakpoints are in-frame and can produce a protein product containing the full kinase domain, i.e., that the breakpoint occurs such that complete triplet codons are intact, and that the RNA sequence will produce a viable protein. The FGR gene fusion can be transfected into cells to confirm that the protein is functionally active with respect to kinase activity and oncogenic activity. cDNA encoding the FGR protein can be produced by standard solid-phase DNA synthesis. Alternatively the FGR fusion cDNA can be produced by RT-PCR using tumor mRNA extracted from samples containing the gene fusion. The DNA amplified can be subcloned into an appropriate vector and characterized by DNA sequence analysis or vitro/in vivo expression analyses.

Expression vectors containing the FGR gene fusion (such as, e.g., WASF2:FGR gene fusion) can be introduced into host cells to thereby produce an FGR protein. The FGR protein expression vector can be a yeast expression vector, a vector for expression in insect cells, e.g., a baculovirus expression vector, or a vector suitable for expression in mammalian cells. Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell.

Cells harboring the expression vector carrying the recombinant FGR gene fusion can then be tested for production of the unique fusion protein via standard Western blotting using either an antibody probe that detects the gene product itself or that recognizes a lag peptide (e.g., FLAG tag) that can be added to the gene product via the expression vector (using standard, commercially available reagents). Western blotting can be used to confirm the ectopic expression of the encoded FGR protein by comparing the samples from cells transfected with the vector containing the FGR gene fusion cDNA to cells transfected with the empty expression vector.

The functional activity can be assessed by measuring the level of phosphorylation on the kinase or substrate. Whether the FGR gene fusion is oncogenic can be assessed by measuring capacity of the expressed FGR protein to transform cells, that is, to enable cells to grow and proliferate under conditions which are not permissive for growth of normal cells. One commonly used method of measuring the transforming activity of a kinase is by assessing if expression of the gene product can allow BaF3 cells to grow in the absence of the growth factor IL3, which is required for the survival and growth of BaF3 cells. Another assay for measuring transforming activity is a soft agar growth assay. This is another standard method which tests the capacity of an introduced gene product to confer the ability to grow in a soft agar matrix, or anchorage-independent conditions. These methods and others can be used to test the oncogenic activity of an FGR gene fusion (such as, e.g., WASF2:FGR gene fusion) as a potential target for treating patients that harbor these fusions.

A change in an activity of a cell can be detected in a cell in culture, e.g., a cell expressing a fusion (e.g., a mammalian cell, a tumor cell or cell line, a recombinant cell). The transfected cell can show a change in response to the expressed fusion, e.g., increased proliferation, changes in morphology, increased tumorigenicity, and/or an acquired transformed phenotype.

To further validate the biological implication of the gene fusion, a change in any of the activities of the cell, e.g., the recombinant cell, in the presence of a known inhibitor of one of the fusion partners, e.g., an FGR inhibitor, can be detected. For example, a decrease in one or more of: proliferation, tumorigenicity, and transformed morphology, in the presence of the BETA inhibitor can be indicative of an inhibitor of a fusion. In other embodiments, a change in binding activity or phosphorylation of FGR or its interacting or downstream proteins or molecules is detected.

All publications and patents mentioned herein are hereby incorporated by reference in their entirety as if each individual publication or patent was specifically and individually indicated to be incorporated by reference. To the extent publications and patents or patent applications incorporated by reference contradict the disclosure contained in the specification, the specification will supersede any contradictory material. Unless otherwise required by context, singular terms shall include the plural and plural terms shall include the singular. The use of "or" means "and/or" unless stated otherwise. The use of the term "including," "having", and "containing," as well as other forms, such as "includes" and "included," "has" and "had," and "contains" and "contained," is not limiting. All ranges given in the application encompass the endpoints unless stated otherwise.

Those skilled in the art will recognize, or be able to ascertain using no more than routine experimentation, many equivalents to the specific embodiments of the invention described herein. Such equivalents are intended to be encompassed by the following claims.

We claim:

1. A method of detecting in a patient a WASF2:FGR gene fusion, said method comprising:
   a) contacting a biological sample from the patient with an oligonucleotide that hybridizes to or amplifies the WASF2:FGR gene fusion of SEQ ID NO:1 or a portion thereof comprising a fusion junction; and
   b) detecting binding between the WASF2:FGR gene fusion and the oligonucleotide or amplification of the WASF2:FGR gene fusion.

2. The method of claim 1, wherein the oligonucleotide hybridizes under stringent conditions to (a) a fragment of SEQ ID NO:1 comprising nucleotides 178-187 of SEQ ID NO:1, or (b) a complementary oligonucleotide of (a).

3. The method of claim 1, wherein the patient is suffering from or susceptible to a cancer.

4. The method of claim 3, wherein the cancer is lung squamous carcinoma, ovarian serous cystadenocarcinoma, cutaneous melanoma, uterine carcinosarcoma, or esophageal carcinoma.

5. The method of claim 4, wherein the cancer is lung squamous carcinoma.

6. The method of claim 4, wherein the cancer is ovarian serous cystadenocarcinoma.

7. The method of claim 4, wherein the cancer is cutaneous melanoma.

8. The method of claim 4, wherein the cancer is uterine carcinosarcoma.

9. The method of claim 4, wherein the cancer is esophageal carcinoma.

* * * * *

SEQUENCE LISTING

```
<160> NUMBER OF SEQ ID NOS: 2

<210> SEQ ID NO 1
<211> LENGTH: 2488
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1
gcccagggcg gggaatcgcg taatggcgga cacaggcagg gcgagcgcgg ctggggcgt        60 agcgcgctga ggggtccgg ccgtttggca gcccgcgagg cggtccgcgg gagcacactc      120
tgtgcggaga ctgggcggcc ggccgaccct tcctgtcgct gacggcgact gcgggaggcc    180
aggtctctga cccctcccaa ggatcatgcc gcagcccac tgacccagga gtagggcct      240 aagggcaggg aacctggaat gggctgtgtg ttctgcaaga aattggagcc ggtggccacg    300
gccaaggagg atgctggcct ggaaggggac ttcagaagct acggggcagc agaccactat    360
gggcctgacc ccactaaggc ccggcctgca tcctcatttg cccacatccc caactacagc    420
aacttctcct ctcaggccat caaccctggc ttccttgata gtggcaccat cagggtgtg     480 tcagggattg gggtgaccct gttcattgcc ctgtatgact atgaggctcg aactgaggat    540
gacctcacct tcaccaaggg cgagaagttc cacatcctga caatactga aggtgactgg     600 tgggaggctc ggtctctcag ctccggaaaa actggctgca ttcccagcaa ctacgtggcc    660
cctgttgact caatccaagc tgaagagtgg tactttggaa agattgggag aaaggatgca    720
gagaggcagc tgctttcacc aggcaacccc caggggcct ttctcattcg ggaaagcgag     780
accaccaaag gtgcctactc cctgtccatc cgggactggg atcagaccag aggcgatcat    840
gtgaagcatt acaagatccg caaactggac atgggcggct actacatcac cacacgggtt    900
```

```
cagttcaact cggtgcagga gctggtgcag cactacatgg aggtgaatga cgggctgtgc    960
aacctgctca tcgcgccctg caccatcatg aagccgcaga cgctgggcct ggccaaggac   1020
gcctgggaga tcagccgcag ctccatcacg ctggagcgcc ggctgggcac cggctgcttc   1080
ggggatgtgt ggctgggcac gtggaacggc agcactaagg tggcggtgaa gacgctgaag   1140
ccgggcacca tgtccccgaa ggccttcctg gaggaggcgc aggtcatgaa gctgctgcgg   1200
cacgacaagc tggtgcagct gtacgccgtg gtgtcggagg agcccatcta catcgtgacc   1260
gagttcatgt gtcacggcag cttgctggat tttctcaaga acccagaggg ccaggatttg   1320
aggctgcccc aattggtgga catggcagcc caggtagctg agggcatggc ctacatggaa   1380
cgcatgaact acattcaccg cgacctgagg gcagccaaca tcctggttgg ggagcggctg   1440
gcgtgcaaga tcgcagactt tggcttggcg cgtctcatca aggacgatga gtacaacccc   1500
tgccaaggtt ccaagttccc catcaagtgg acagcccag aagctgccct ctttggcaga   1560
ttcaccatca gtcagacgt gtggtccttt gggatcctgc tcactgagct catcaccaag   1620
ggccgaatcc cctacccagg catgaataaa cgggaagtgt tggaacaggt ggagcagggc   1680
taccacatgc cgtgccctcc aggctgccca gcatccctgt acgaggccat ggaacagacc   1740
tggcgtctgg acccggagga gaggcctacc ttcgagtacc tgcagtcctt cctggaggac   1800
tacttcacct ccgctgaacc acagtaccag cccggggatc agacatagcc tgtccgggca   1860
tcaaccctct ctggcggtgg ccaccagtcc ttgccaatcc ccagagctgt tcttccaaag   1920
cccccaggct ggcttagaac cccatagagt cctagcatca ccgaggacgt ggctgctctg   1980
acaccaccta gggcaaccta cttgttttac agatggggca aaaggaggcc cagagctgat   2040
ctctcatccg ctctggcccc aagcactatt tcttcctttt ccacttaggc ccctacatgc   2100
ctgtagcctt tctcactcca tccccaccca aagtgctcag accttgtcta gttatttata   2160
aaactgtatg tacctccctc acttctctcc tatcactgct ttcctactct ccttttatct   2220
cactctagtc caggtgccaa gaatttccct tctaccctct attctcttgt gtctgtaagt   2280
tacaaagtca ggaaaagtct tggctggacc ccttccctgc tgggtggatg cagtggtcca   2340
ggactggggt ctgggcccag gtttgaggga gaaggttgca gagcacttcc cacctctctg   2400
aatagtgtgt atgtgttggt ttattgattc tgtaaataag taaatgaca atatgaatcc   2460
tcaaaccatg aaaaaaaaaa aaaaaaaa                                      2488
```

<210> SEQ ID NO 2
<211> LENGTH: 529
<212> TYPE: PRT
<213> ORGANISM: Homo sapiens

<400> SEQUENCE: 2

Met Gly Cys Val Phe Cys Lys Lys Leu Glu Pro Val Ala Thr Ala Lys
1               5                   10                  15

Glu Asp Ala Gly Leu Glu Gly Asp Phe Arg Ser Tyr Gly Ala Ala Asp
            20                  25                  30

His Tyr Gly Pro Asp Pro Thr Lys Ala Arg Pro Ala Ser Ser Phe Ala
        35                  40                  45

His Ile Pro Asn Tyr Ser Asn Phe Ser Ser Gln Ala Ile Asn Pro Gly
    50                  55                  60

Phe Leu Asp Ser Gly Thr Ile Arg Gly Val Ser Gly Ile Gly Val Thr
65                  70                  75                  80

Leu Phe Ile Ala Leu Tyr Asp Tyr Glu Ala Arg Thr Glu Asp Asp Leu

```
                85                  90                  95
Thr Phe Thr Lys Gly Glu Lys Phe His Ile Leu Asn Asn Thr Glu Gly
            100                 105                 110

Asp Trp Trp Glu Ala Arg Ser Leu Ser Ser Gly Lys Thr Gly Cys Ile
            115                 120                 125

Pro Ser Asn Tyr Val Ala Pro Val Asp Ser Ile Gln Ala Glu Glu Trp
            130                 135                 140

Tyr Phe Gly Lys Ile Gly Arg Lys Asp Ala Glu Arg Gln Leu Leu Ser
145                 150                 155                 160

Pro Gly Asn Pro Gln Gly Ala Phe Leu Ile Arg Glu Ser Glu Thr Thr
                165                 170                 175

Lys Gly Ala Tyr Ser Leu Ser Ile Arg Asp Trp Asp Gln Thr Arg Gly
            180                 185                 190

Asp His Val Lys His Tyr Lys Ile Arg Lys Leu Asp Met Gly Gly Tyr
            195                 200                 205

Tyr Ile Thr Thr Arg Val Gln Phe Asn Ser Val Gln Glu Leu Val Gln
            210                 215                 220

His Tyr Met Glu Val Asn Asp Gly Leu Cys Asn Leu Leu Ile Ala Pro
225                 230                 235                 240

Cys Thr Ile Met Lys Pro Gln Thr Leu Gly Leu Ala Lys Asp Ala Trp
                245                 250                 255

Glu Ile Ser Arg Ser Ser Ile Thr Leu Glu Arg Arg Leu Gly Thr Gly
            260                 265                 270

Cys Phe Gly Asp Val Trp Leu Gly Thr Trp Asn Gly Ser Thr Lys Val
            275                 280                 285

Ala Val Lys Thr Leu Lys Pro Gly Thr Met Ser Pro Lys Ala Phe Leu
            290                 295                 300

Glu Glu Ala Gln Val Met Lys Leu Leu Arg His Asp Lys Leu Val Gln
305                 310                 315                 320

Leu Tyr Ala Val Val Ser Glu Glu Pro Ile Tyr Ile Val Thr Glu Phe
                325                 330                 335

Met Cys His Gly Ser Leu Leu Asp Phe Leu Lys Asn Pro Glu Gly Gln
            340                 345                 350

Asp Leu Arg Leu Pro Gln Leu Val Asp Met Ala Ala Gln Val Ala Glu
            355                 360                 365

Gly Met Ala Tyr Met Glu Arg Met Asn Tyr Ile His Arg Asp Leu Arg
            370                 375                 380

Ala Ala Asn Ile Leu Val Gly Glu Arg Leu Ala Cys Lys Ile Ala Asp
385                 390                 395                 400

Phe Gly Leu Ala Arg Leu Ile Lys Asp Asp Glu Tyr Asn Pro Cys Gln
                405                 410                 415

Gly Ser Lys Phe Pro Ile Lys Trp Thr Ala Pro Glu Ala Ala Leu Phe
            420                 425                 430

Gly Arg Phe Thr Ile Lys Ser Asp Val Trp Ser Phe Gly Ile Leu Leu
            435                 440                 445

Thr Glu Leu Ile Thr Lys Gly Arg Ile Pro Tyr Pro Gly Met Asn Lys
            450                 455                 460

Arg Glu Val Leu Glu Gln Val Glu Gln Gly Tyr His Met Pro Cys Pro
465                 470                 475                 480

Pro Gly Cys Pro Ala Ser Leu Tyr Glu Ala Met Glu Gln Thr Trp Arg
                485                 490                 495

Leu Asp Pro Glu Glu Arg Pro Thr Phe Glu Tyr Leu Gln Ser Phe Leu
            500                 505                 510
```

```
Glu Asp Tyr Phe Thr Ser Ala Glu Pro Gln Tyr Gln Pro Gly Asp Gln
        515                 520                 525
Thr
```